(12) United States Patent
Martin et al.

(10) Patent No.: US 6,490,913 B1
(45) Date of Patent: Dec. 10, 2002

(54) HUMIDITY CHAMBER FOR SCANNING STYLUS ATOMIC FORCE MICROSCOPE WITH CANTILEVER TRACKING

(75) Inventors: Jonathan W. Martin, Montgomery Village; Edward Embree, Frederick; Mark R. VanLandingham, Gaithersburg, all of MD (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 0 days.

(21) Appl. No.: 09/573,277

(22) Filed: May 18, 2000

Related U.S. Application Data
(60) Provisional application No. 60/134,885, filed on May 19, 1995.

(51) Int. Cl.[7] ........................... G01B 11/30; G01B 21/30
(52) U.S. Cl. ......................................... 73/105; 73/865.6
(58) Field of Search ............................... 73/105, 865.6; 250/306, 307

(56) References Cited

U.S. PATENT DOCUMENTS

| | | | |
|---|---|---|---|
| 4,301,252 A | 11/1981 | Baker et al. | 439/290 |
| 4,892,830 A | 1/1990 | Findley et al. | 435/250 |
| 5,289,004 A | 2/1994 | Okada et al. | 250/306 |
| 5,291,775 A | 3/1994 | Gamble et al. | 73/105 |
| 5,353,115 A | * 10/1994 | McIntyre | 356/358 |
| 5,388,452 A | 2/1995 | Harp et al. | 73/105 |
| 5,393,980 A | 2/1995 | Yost et al. | 250/306 |

(List continued on next page.)

FOREIGN PATENT DOCUMENTS

| WO | WO 99/62097 | 12/1999 | ............ H01J/37/00 |
|---|---|---|---|

OTHER PUBLICATIONS

Atomic Force Microscope Hindered in Liquid, Photon. Spec. (Laurin Pub. Co.) (Sep. 1997), 1 page.
The Atomic Force Microscope, <http://www.sst.ph.ic.ac.uk/photonics/intro/AFM.html> (Apr. 2000), 2 pages.
Terra, R., Manipulating Atoms and Molecules With the Scanning Tunneling Microscope and Atomic Force Microscope, Nano. Tech. Mag. (1998), Month not given, 8 pages.

*Primary Examiner*—Thomas P. Noland
(74) *Attorney, Agent, or Firm*—Kilpatrick Stockton LLP; Alana G. Kriegsman, Esq.; Cynthia B. Rothschild, Esq.

(57) ABSTRACT

The present invention provides a novel humidity chamber suitable for use with an atomic force microscope (AFM). The humidity chamber of the present invention employs an intricate geometrical design which can accommodate a scanned-stylus AFM with an optical lever. This geometrical design allows the invention to enclose one or more of the AFM scanner, tip assembly, optical lever detection system, sample and an optical microscope objective lens, without degrading the ability to operate the AFM or the related systems. The invention is comprised of two major pieces: a chamber within which the AFM scanning head assembly is placed, and an integrated sample platform and spring-loaded base-plate that allows samples to be loaded and unloaded without removal of the chamber from the AFM scanning head assembly. The sample platform, which extends up from the base-plate and is inserted into the chamber, can include a magnet that is securely attached to the base. Once the sample platform is positioned inside the chamber, a locking pin can be inserted between the chamber and the bottom portion of the sample platform to secure the sample platform and base-plate. The spring-loaded base allows the z-directional motors of the AFM to be used to position the sample just below the probe prior to scanning, while at the same time providing an essentially air-tight fit between the chamber and the AFM scanning head. An embodiment of the present invention is suitable for use with components that sense and control the relative humidity inside the chamber.

20 Claims, 5 Drawing Sheets

U.S. PATENT DOCUMENTS

| | | | |
|---|---|---|---|
| 5,440,920 A | 8/1995 | Jung et al. | 73/105 |
| 5,463,897 A | 11/1995 | Prater et al. | 73/105 |
| 5,560,244 A | 10/1996 | Prater et al. | 73/105 |
| 5,587,523 A | 12/1996 | Jung et al. | 73/105 |
| 5,675,154 A | 10/1997 | Lindsay et al. | 250/306 X |
| 5,714,682 A | 2/1998 | Prater et al. | 73/105 |
| 5,744,704 A * | 4/1998 | Hu et al. | 73/105 |
| 5,760,396 A | 6/1998 | Lindsay et al. | 250/306 |
| 5,763,767 A | 6/1998 | Jung et al. | 71/105 |
| 5,804,709 A * | 9/1998 | Bourgein et al. | 73/105 |
| 5,821,545 A | 10/1998 | Lindsay et al. | 250/445.1 |
| 5,825,020 A | 10/1998 | Hansma et al. | 250/306 X |
| 5,831,153 A | 11/1998 | Binnig et al. | 73/105 |
| 5,861,550 A | 1/1999 | Ray | 73/105 |
| 5,874,669 A | 2/1999 | Ray | 73/105 |
| 6,021,665 A | 2/2000 | Hayashi et al. | 73/105 |
| 6,032,518 A | 3/2000 | Prater et al. | 73/105 |
| 6,051,825 A | 4/2000 | Lindsay et al. | 250/306 X |
| 6,180,415 B1 * | 1/2001 | Schultz et al. | 436/518 |
| 6,194,813 B1 * | 2/2001 | Israelachvii | 310/328 |
| 6,242,291 B1 * | 6/2001 | Kusumoto et al. | 438/158 |
| 2001/0008272 A1 * | 7/2001 | Rinn | 73/105 X |
| 2002/0001544 A1 * | 1/2002 | Hess et al. | 422/100 |

\* cited by examiner

HUMIDITY CHAMBER FOR SCANNING STYLUS ATOMIC FORCE MICROSCOPE WITH CANTILEVER TRACKING

CROSS REFERENCE TO RELATED APPLICATIONS

This application claims the benefit of applicants' co-pending application having U.S. Ser. No. 60/134,885 filed May 19, 1999.

STATEMENT OF GOVERNMENT INTEREST

The invention described herein was made in the performance of official duties by employees of the United States of America as represented by the Secretary of Commerce, National Institute of Standards and Technology and, thus, the invention disclosed herein may be manufactured, used, and licensed by or for the Government for governmental purposes without the payment of any royalties thereon.

FIELD OF THE INVENTION

The present invention relates to environmental control for atomic force microscopes, and in particular to controlling the humidity level of the environment local to the probe and sample during scanning with a scanning stylus atomic force microscope.

BACKGROUND OF THE INVENTION

The Atomic Force Microscope, or AFM, allows high-resolution imaging at the subnanometer level, and in a liquid environment at the atomic level. The basic objective of the operation of the AFM is to measure the forces (at the atomic level) between a sharp probing tip (which is attached to a cantilever spring) and a sample surface. Images are taken by scanning the sample relative to the probing tip and measuring the deflection of the cantilever as a function of lateral position. The AFM probe is scanned across the sample surface to generate an image. As the scan progresses the AFM measures the small upward and downward movements that are needed to maintain a constant force of contact. Because the AFM senses the surface by "touch", it allows imaging of nonconducting materials such biological and molecules, plastics, ceramics, and insulating materials like glass or diamond, with nanometer resolution.

Because of its unique capabilities, the AFM is widely recognized as an important tool for evaluating materials and materials-enabled engineering systems. In particular, the ability to image materials in a variety of environments, including under ambient conditions and in liquids, enables high resolution imaging of biomaterials and polymers without causing significant deterioration of the materials or introducing artifacts related to the extensive sample preparation used in other high resolution microscopes. However, during imaging in ambient conditions, surface contamination will occur due to the presence of moisture in the form of humidity that will adsorb onto the sample surface. The amount of adsorbed moisture, which will depend on the ambient relative humidity, can affect AFM imaging and force measurements. When the tip of the AFM probe scans over a moist sample, it sometimes takes a hopping motion because of the way the water molecules are layered. This hopping motion, is believed to affect a sample's image quality. Therefore, controlling the humidity level during scanning becomes an important factor when using the AFM.

To date, it is believed that only one commercially available humidity chamber exists for use with an AFM. The existing commercially available humidity chamber, however, is limited to a particular type of scanned sample AFMs, where the AFM probe and detection system are fixed and the sample is moved by the scanners. Thus, the currently available humidity chamber is limited to scanned sample AFMs and cannot be used with scanned stylus AFMs, where the sample is fixed and the probe is rastered across the sample by the scanners. The head of the scanned stylus AFM has a much more complicated geometric design than the scanned sample AFM, thus rendering the design of a humidity chamber a much more difficult task.

The present invention, however, overcomes these problems and provides a humidity chamber which can be used in conjunction with a scanned stylus AFM, and similar microscopes.

SUMMARY OF INVENTION

It is an object of the present invention to provide a novel humidity chamber suitable for use with a scanned stylus atomic force microscope (AFM) and similar microscopes.

It is a further object of the present invention to provide a novel humidity chamber comprising a novel geometrical design configured to accommodate a scanned-stylus AFM having an optical lever.

It is a further object of the present invention to provide a humidity chamber suitable for use with a scanned stylus AFM which also provides for full enclosure of one or more of the AFM scanner, tip assembly, optical lever detection system, sample, and side-mounted optical microscope objective lens (camera), without degrading the ability to operate the AFM or the related systems.

It is a further object of the present invention to provide a humidity chamber suitable for use with a scanned stylus AFM, wherein the humidity chamber comprises a chamber, a spring loaded base and a side entry port.

It is a further object of the present invention to provide a humidity chamber suitable for use with a scanned stylus AFM which allows samples to be loaded and unloaded without removal of the chamber from the AFM scanning head assembly.

It is a further object of the present invention to provide a humidity chamber suitable for use with a scanned stylus AFM which provides a snug, essentially air-tight, fit between the chamber and the AFM scanning head assembly.

It is a further object of the present invention to provide a humidity chamber suitable for use with a scanned stylus AFM which provides easy access to an optical microscope lens.

It is a further object of the present invention to provide a humidity chamber suitable for use with a scanned stylus AFM which allows for the use of an optical system.

It is a further object of the present invention to provide a humidity chamber suitable for use with a scanned stylus AFM which allows for the use of an optical system to locate and focus on a probe and/or sample surface.

It is a further object of the present invention to provide a humidity chamber suitable for use with a scanned stylus AFM which allows humid air to be delivered into the chamber, fill the chamber, and exit the chamber.

It is a further object of the present invention to provide a humidity chamber suitable for use with a scanned stylus AFM which both allows the z-directional motors of the AFM to be used to position the sample just below the probe (scanning tip) prior to scanning, and provides a snug fit between the chamber and the AFM scanning head.

It is a further object of the present invention to provide a humidity chamber suitable for use with a scanned stylus AFM which allows precise control of relative humidity.

These and other objects are achieved according to the present invention by providing a new and improved a humidity chamber which can be used to provide a humidity-free environment, or alternatively a humidity intense environment (humidity level can be maintained at a specified level) suitable for use with a scanned stylus AFM. The invention generally comprises a chamber within which the AFM scanning head assembly is placed, and an integrated sample platform and spring-loaded base-plate that allow samples to be loaded and unloaded without removal of the humidity chamber from the AFM scanning head assembly. Once the sample platform is positioned inside the chamber, a locking clip is inserted between the chamber and the bottom portion of the sample platform to secure the sample platform and base-plate. The spring-loaded base allows the z-directional motors of the AFM to be used to position the sample just below the AFM scanning tip (probe) prior to scanning, while at the same time providing a snug fit between the chamber and the AFM scanning head.

In an embodiment of the present invention, the humidity chamber comprises a chamber of specified geometry within which the AFM scanning head assembly is placed, and an integrated sample platform and spring-loaded base-plate which allow samples to be loaded and unloaded without removal of the chamber from the AFM scanning head assembly.

In an embodiment of the present invention, the humidity chamber comprises a chamber of specified geometry which allows the use of an optical system to locate and focus on a probe and/or sample surface.

In an embodiment of the present invention, the humidity chamber includes adjacent entry and exit ports that allow humid air to be delivered into the chamber, fill the chamber, and exit the chamber.

In an embodiment of the present invention, the sample platform extends up from the base-plate and is inserted into the chamber, and includes a magnetic sample port comprising a magnet securely attached to the base-plate.

In an embodiment of the present invention, a locking pin secures the sample platform and base-plate once the sample platform is positioned inside the chamber.

In an embodiment of the present invention, the humidity chamber includes a port configured to allow for the use of an optical system.

In an embodiment of the present invention, the humidity chamber includes a large side-entry port configured to allow access to an optical microscope lens.

In an embodiment of the present invention, one or more of the AFM scanner, tip assembly (probe), optical lever detection system, sample, and side-mounted optical microscope objective lens (camera) are fully enclosed.

In an embodiment of the present invention, a magnetic sample port is configured to provide a snug fit between the chamber and the AFM scanning head assembly.

BRIEF DESCRIPTION OF DRAWINGS

A more complete appreciation of the invention and the attendant advantages thereof will be readily obtained as the same becomes better understood by reference to the following detailed description when considered in connection with the accompanying drawings, wherein:

FIGS. 1 and 2 provide prospective views of the humidity chamber of the present invention. In FIG. 2, the integrated sample platform and base are shown removed from the chamber.

FIGS. 7–11 provide engineering drawings of an embodiment of the humidity chamber of the present invention configured to accommodate a scanned-stylus AFM having an optical lever such as that described in U.S. Pat. Nos. 6,032,518; 5,714,682; 5,560,244; and 5,463,897.

DETAILED DESCRIPTION OF THE INVENTION

The present invention comprises a humidity chamber which can be used to provide a humidity-free environment, or alternatively a humidity intense environment in which a specified humidity level can be maintained. The humidity chamber of the present invention is suitable for use with an atomic force microscope (AFM), or other commercially available microscopes. A preferred embodiment of the humidity chamber of the present invention employs an intricate geometrical design which accommodates a scanned-stylus AFM having an optical lever such as that described in U.S. Pat. Nos. 6,032,518; 5,714,682; 5,560,244; and 5,463,897. The geometrical design of the humidity chamber of the present invention allows the AFM scanner, tip assembly (probe), optical lever detection system, sample, and if necessary, a side-mounted optical microscope objective lens (camera), to be fully enclosed without degrading significantly the ability to operate the AFM or the related systems.

The invention generally comprises a means for using, and for accessing, an optical system to locate and focus on one of more of a probe and a sample surface, the means preferably including, but not limited to, a chamber within which the AFM scanning head assembly is placed, an integrated sample platform, and a spring-loaded base-plate that allows samples to be loaded and unloaded without removal of the chamber from the AFM scanning head assembly. Once the sample platform is positioned inside the chamber, a locking pin can be inserted between the chamber and the bottom portion of the sample platform to secure the sample platform and base-plate. The invention includes means for using an optical system to locate and focus on one or more of a probe and sample surface, the means preferably including, but not limited to, a spring-loaded base which allows the z-directional motors of the AFM to be used to position the sample just below the probe prior to scanning while at the same time providing a snug fit between the chamber and the AFM scanning head. An embodiment of the present invention is also suitable for use with a means for controlling relative humidity, such as a humidity-generating device, (for instance, the humidity generator manufactured by VTI Corporation), which allows precise control of relative humidity. Use of the invention with a humidity generating device has shown large differences in force measurements made on mica at several different humidity levels. An embodiment of the present invention is also suitable for use with a means for sensing relative humidity, such as a commercially available humidity-sensing device, (for instance, the Thin-Film Capacitance Sensor manufactured by Vaisala).

Figure 1:
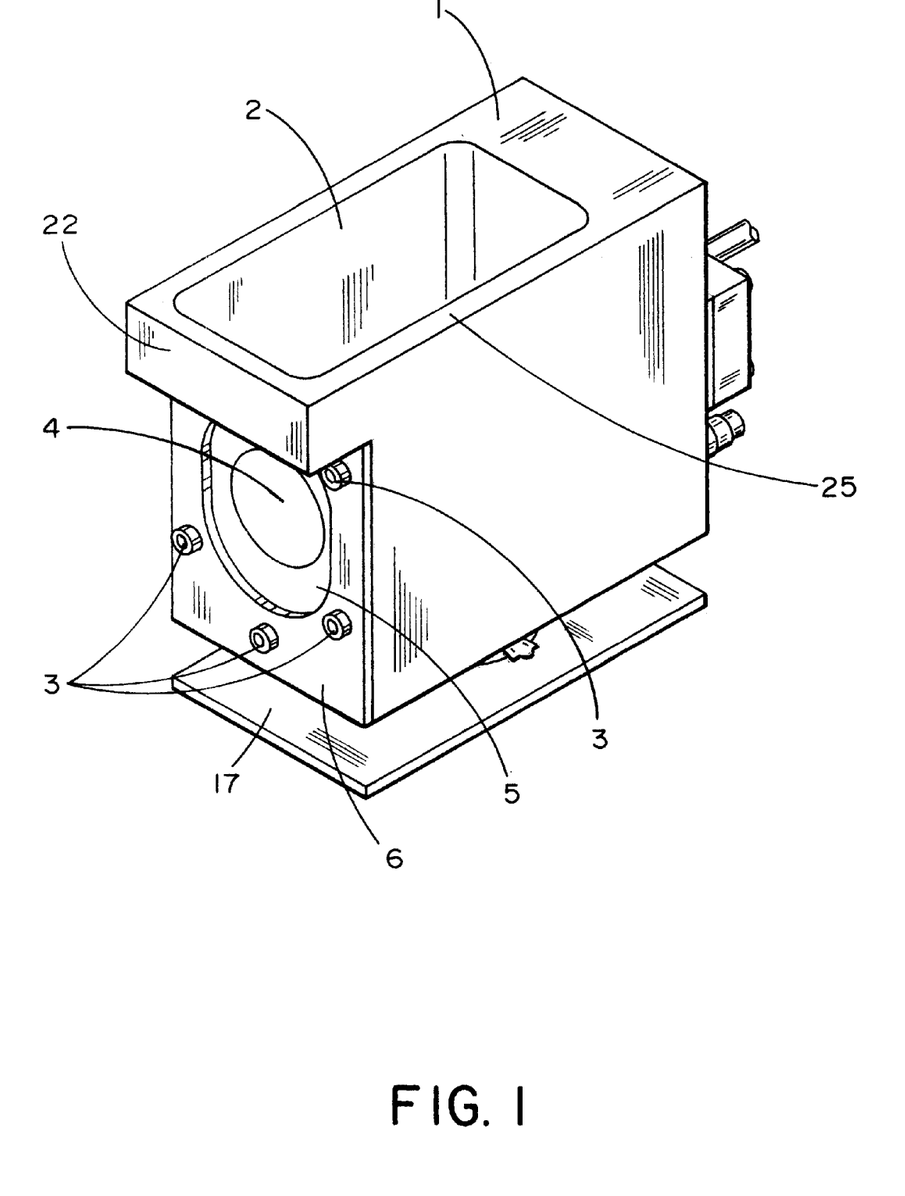
Figure 2:
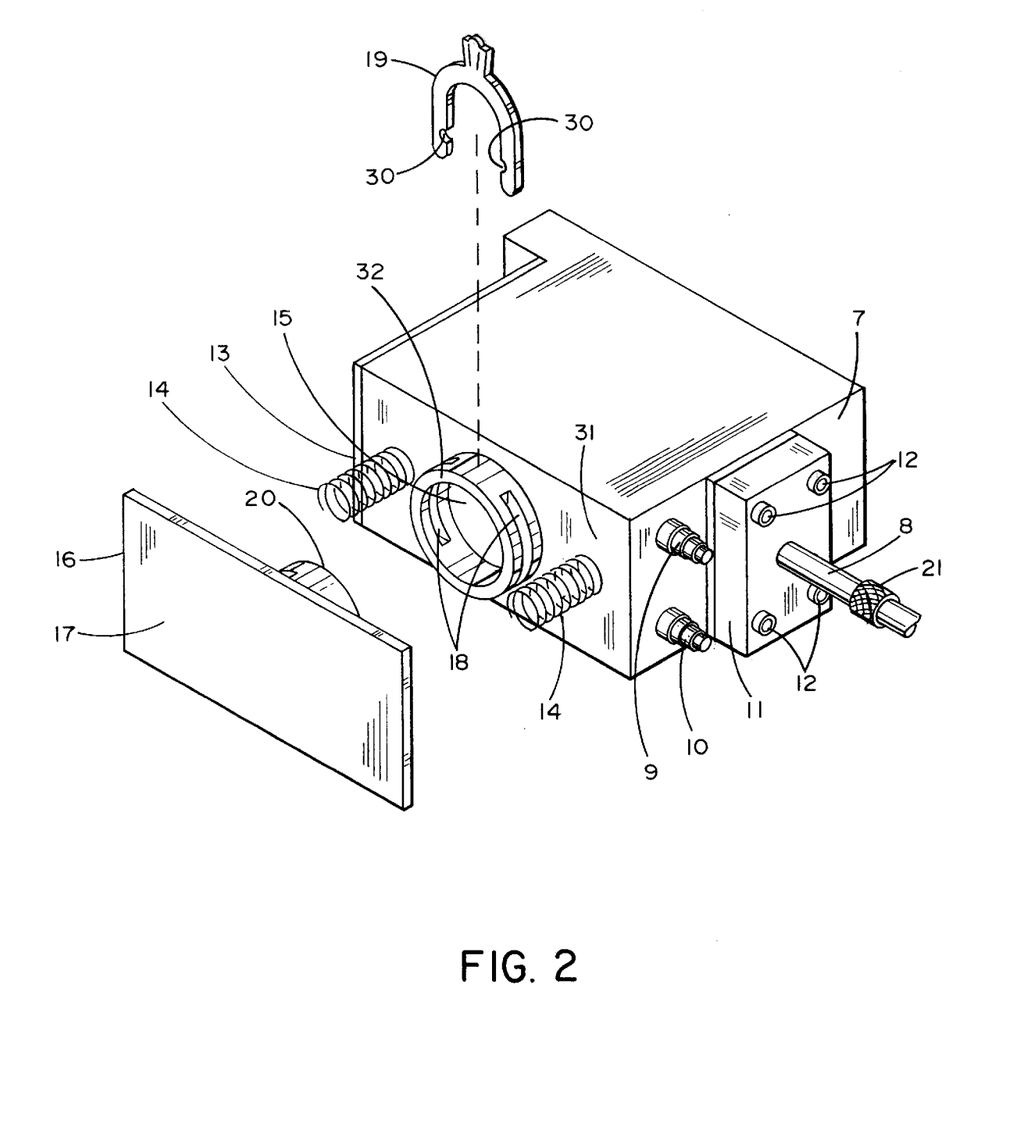
Figure 3:
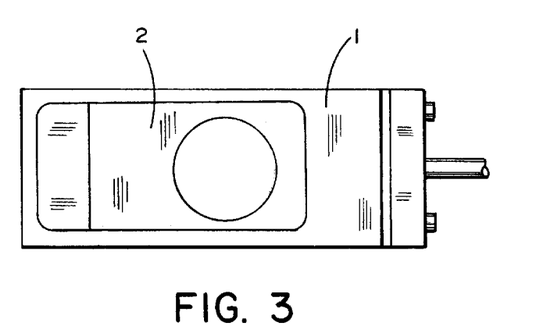
FIGS. 3–6 provide block views of the top, sides, and front of the humidity chamber of the present invention.
Figures 4, 5, 6:
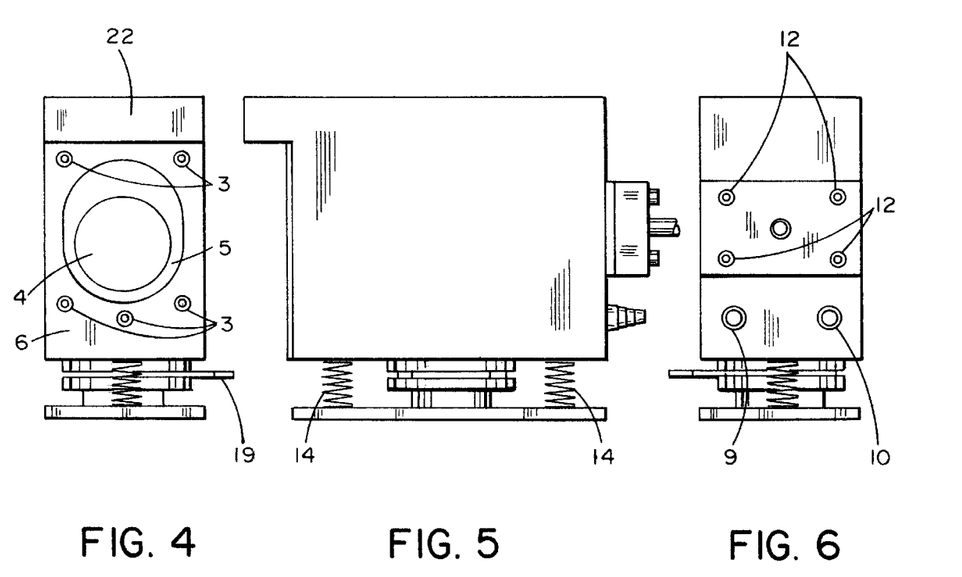

An embodiment of the present invention is shown in FIGS. 1 through 11. Specifically, FIGS. 1 and 2 present perspective views of the chamber of the present invention. FIGS. 3–6 presents two-dimensional side, top, bottom, front, and back views of the humidity chamber.

The chamber of the present invention is preferably constructed of Teflon. The top of the chamber 1 is open to allow insertion of the AFM scanning head assembly. The opening (port) 2 is uniquely geometrically configured so as to envelope the head and provide a snug and essentially air tight fit while allowing normal operation of the AFM. A snug and essentially air tight fit is achieved through the use of a precisely-sized opening 2 relative to the AFM scanning head assembly, and/or a rubber membrane or gasket (not shown). A side-entry port 4 at the left side of the chamber allows for insertion of the AFM optical microscope objective lens (camera). A rubber membrane or gasket 5 is provided around the camera port 4 in order to facilitate a snug and essentially air tight fit here also, while allowing normal operation of the AFM. The rubber membrane or gasket 5 can be held in place by use of a membrane retainer plate 6 and screws 3, as shown in FIG. 1, or any other suitable means.

The chamber of the present invention can be used with any type of AFM, or microscope generally, so long as ports 2 and 4 are adapted to conform to the particular AFM or microscope to provide a snug and essentially air-tight fit while allowing normal operation of the AFM or microscope. The overall dimensions of the humidity chamber are not critical. However, because the humidity chamber "sits" on the stage of the AFM or microscope, the overall dimensions of the humidity chamber are limited by the constraints of the particular AFM or microscope selected. In one embodiment, for instance, the top of the chamber includes an optional lip 22 which matches a lip on the head of the scanned-stylus AFM described in U.S. Pat. Nos. 6,032,518; 5,714,682; 5,560,244; and 5,463,897.

The right side 7 of the humidity chamber of the present invention is adapted to allow the use of a commercially available humidity sensor (not shown), such as the Thin-Film Capacitance Sensor manufactured by Vaisala, and a commercially available humidity generator (not shown), such as the humidity generator manufactured by VTI Corporation. Specifically, the chamber is adapted to include means for receiving and retaining signals from the humidity sensor, the means preferably being, but not limited to, a two-wire cable 8 which can take humidity readings from the chamber and transmit the readings to the humidity generator. Such a cable ("a humidity sensor") is generally included as part of commercially available humidity sensing devices. The chamber is adapted to receive the humidity sensor 8 securely.

A secure attachment of the humidity sensor 8 to the chamber is facilitated by the use of a mounting mechanism constructed of a block 11 of Teflon, or other suitable material, which is attached to the side of the chamber by screws 12, and which includes a threaded hole (not shown) adapted to allow the threaded end 21 of the humidity sensor 8 to be screwed in place. The use of such a mounting mechanism is preferable due to the thinness of the walls of the humidity chamber. Other suitable mounting means, of course, would be within the scope of the present invention and might be more appropriate depending on the configuration of a particular humidity sensor.

The right side of the chamber is constructed to allow for attachment of a conditioned air input 9 tube and a conditioned air output 10 tube from a commercially available humidity generator (tubes are not shown). Attachment can be facilitated by any appropriate means, such as the use of appropriately sized hose-barbs 9 and 10 as shown in FIGS. 1–6. Other appropriate attachment mechanisms would include screws, or the like.

In a preferred embodiment, the present invention includes an integrated sample platform and a spring loaded base-plate. Specifically, the bottom 13 of the chamber includes a sample porthole 15 and one or more compression springs 14 mounted to the bottom of the chamber, one on each side of the sample porthole 15. The sample porthole 15 is appropriately shaped to facilitate insertion of a separate sample platform 16. The sample platform 16 contains a sample stage 20 which extends up from a base-plate 17 and which can be inserted into the chamber via the sample porthole 15. The base-plate 17 of the sample platform 16 is of an appropriate size so as to be able to "sit" on the stage (not shown) of the selected AFM or microscope.

The sample stage 20 is adaptable for particular types of samples (not shown). The sample can be set on the sample stage 20 after the sample platform 16 is inserted in the sample porthole 15 and the locking clip 19 is in place over the sample porthole 15, thereby allowing for samples to be loaded and unloaded without removal of the entire chamber. Obviously, the AFM, or microscope, head assembly is not in the chamber at the time of the insertion of the sample. Preferably, the AFM optical microscope objective lens, or camera, is also not in place in the side-port 4 at the time of the insertion of the sample. Alternatively, after the chamber is secured to the AFM, or microscope, head assembly, the entire chamber-head assembly unit can be raised up by raising the head assembly in the normal fashion, and a the sample stage 20 dropped out for insertion of a new sample.

The upper portion of the sides of the sample porthole 15 include cut-outs (or grooves) 18 configured to facilitate insertion of a separate retaining clip 19 (a "locking clip" 19) which, when in place, locks the sample platform 16 into the sample porthole 15. After the sample platform 16 is inserted in the sample porthole 15, the locking clip 19 is inserted over the sample porthole 15, such that the notched portions 30 of the locking clip 19 are inserted in the cut-outs 18 of the sample port-hole 16 thereby holding the sample platform 16 in place. The sample stage retaining clip 19 can be made of any suitable material, such as stainless steel. The base-plate 17 of the sample platform 16 can optionally include a magnet (not shown) attached to the base-plate 17 to assist in securing the sample platform 16 to the sample porthole 15 prior to insertion of the locking clip 19. In an alternative locking mechanism, the upper 0.1875 in. of the sample platform has a larger diameter than the lower 0.375 in. (see FIG. 8). This feature allows an alternative u-shaped locking pin (not shown in the figures), to be inserted into edge notches in the porthole (see FIG. 7), thereby keeping the sample platform from falling back out of the chamber.

When the sample stage retaining clip 19 is in place, the compression springs 14 are slightly compressed, and the base-plate 17 of the sample platform 16 is a distance apart from the base 31 of the chamber. The compression springs 14 act to keep the sample platform 16 from moving further up into the chamber. However, additional force can be applied to the base-plate 17 of the sample platform 16 to move the sample platform further up into the chamber. Alternatively, the sample platform 16 can move up from the point where the sample stage retaining clip 19 holds the sample platform 16 in the chamber, at which time the base-plate 17 of the sample platform 16 will come into contact with the bottom edge 32 of the sample porthole 15 and the compression springs 14 will be almost fully compressed.

During normal operation of the AFM, the AFM head assembly is lowered in very small increments towards the sample. When the chamber of the present invention is in place, however, as the head of the AFM is lowered in its normal manner, the sample platform 16 is pushed downwards against the compression springs 14 thereby causing the sample platform 16 to move up towards the AFM scanning probe. Thus, a means for positioning a sample prior to scanning is provided in which the normal operation of the z-directional motor of the AFM can be used to position the sample just below the AFM scanning probe tip prior to scanning.

The use of chamber walls 25 which are thicker than those shown in the preferred embodiment is within the scope of the present invention and in fact may be preferable in that thicker walls will better insulate the chamber, which may be desirable. Alternatively, insulation can be achieved by the use of heat pads, or a heating element, applied to the chamber (not shown). For instance, in situation where a heated environment is desired, warm air with a controlled relative humidity percentage (if desired), can be blown into the chamber through the conditioned air input 9 port, and in order to avoid condensation, the chamber can be maintained at the same temperature by the application of heating pads, or heating elements, to the outside of the chamber.

EXAMPLE

Figure 7:
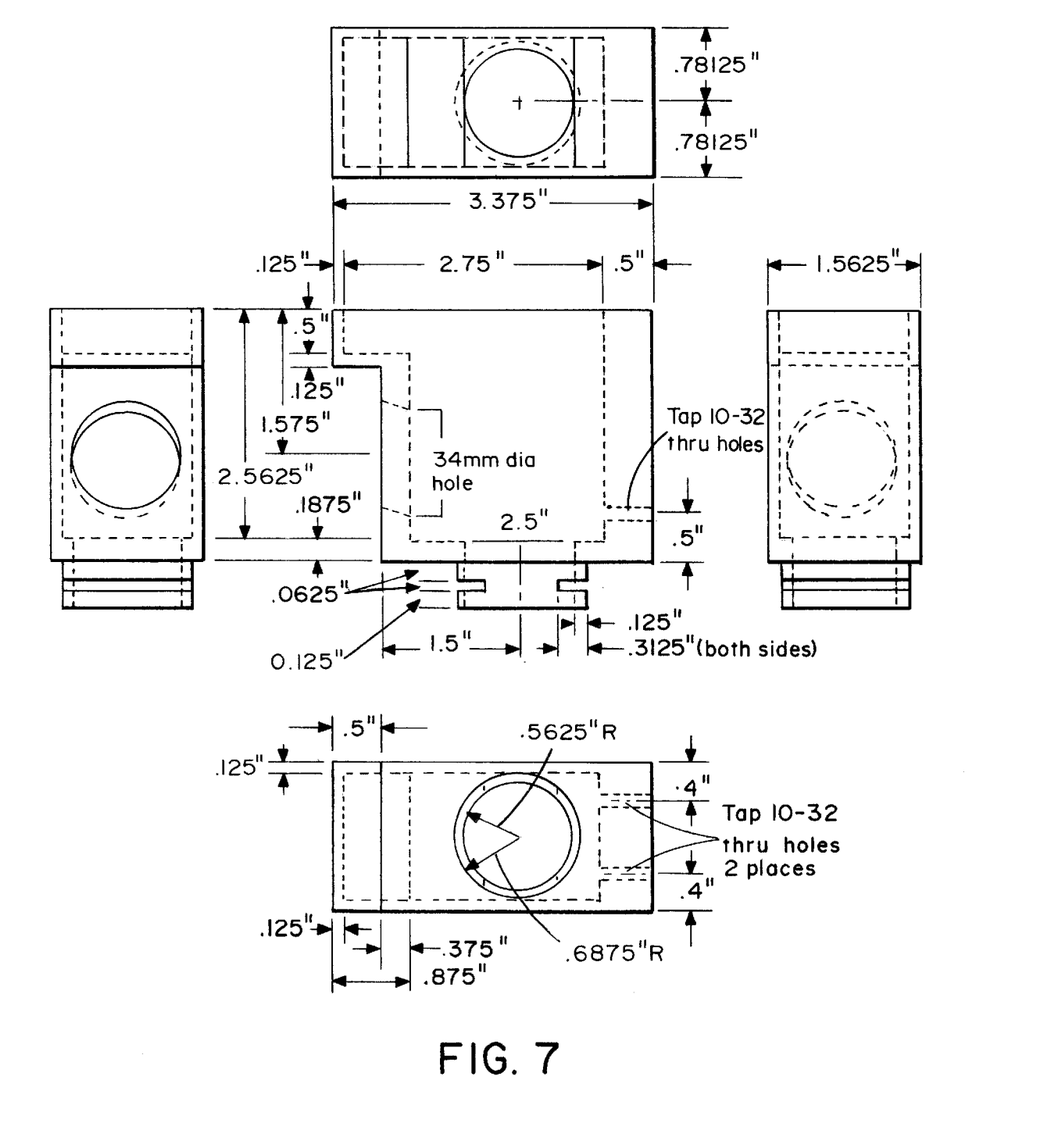
Figure 8:
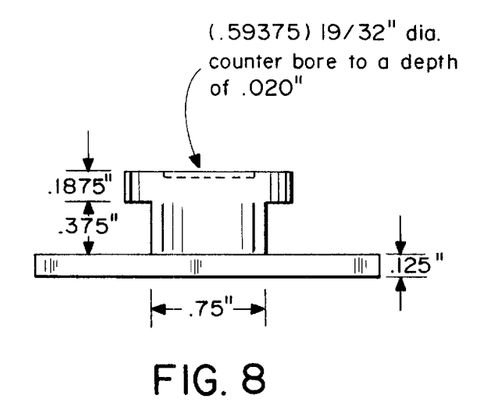
FIGS. 8–10 provide engineering drawings of the integrated sample platform and base (the spring positions and magnet are not shown).
Figure 9:
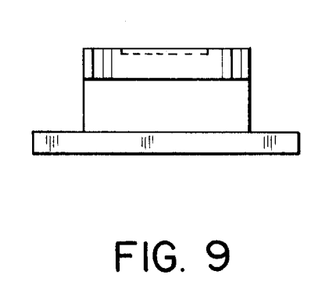
Figure 10:
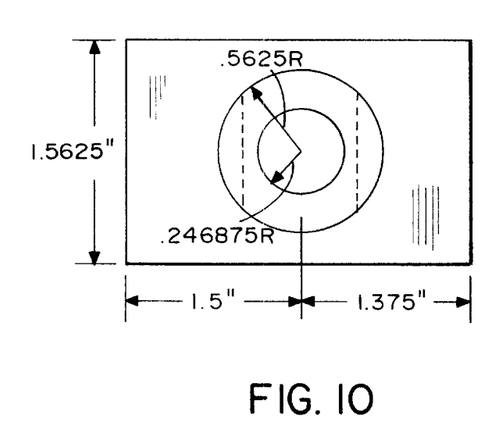
Figure 11:
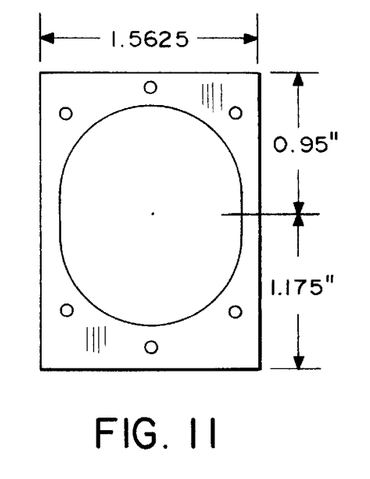
FIG. 11 provides an engineering drawing of a securing plate used to mount a rubber strip used as a seal around the optical microscope lens.

FIGS. 7–11 provide the precise dimensions of an embodiment of the humidity chamber configured to accommodate a scanned-stylus AFM such as that manufactured by Digital Instruments, or as described in U.S. Pat. Nos. 6,032,518; 5,714,682; 5,560,244; and 5,463,897. In FIG. 7, a hole in the front of the chamber is shown which accommodates the particular optical system used on a current commercially available scanned stylus AFM similar to that described in the aforementioned U.S. Patents. This particular optical system contains a camera with an objective lens that is positioned at an angle approximately 15° from the horizontal plane. Note that the hole in the chamber has a larger diameter than the camera lens. To seal the chamber around the lens, a 2 mm thick piece of silicon rubber (not shown) is mounted on the front of the chamber with the securing plate shown in FIG. 11. The securing plate has a hole with dimensions larger than the camera lens, but the diameter of the hole in the silicon rubber is slightly smaller than the camera lens, so that the rubber fits snugly around the camera lens to prevent air from escaping. The securing plate and silicon rubber sheet are fastened to the front of the chamber under the overhang (see FIG. 7) using screws in the positions indicated in FIG. 11. Two holes are tapped through the back wall of the chamber, as shown in FIG. 7. These holes are entry and exit ports for humid air to flow into and out of the chamber. Thus, humid air, presumably with a controlled relative humidity percentage, can come in through the entry port and fill up the chamber volume as the ambient air evacuates through the exit port. This process will continue until an equilibrium humidity level is reached in the chamber, at which time, the humid air will continue to flow steadily through the entry port, into the chamber, and out the exit port.

While the present invention has been described with reference to several specific embodiments, those skilled in the art will be able to make various modifications to the described embodiments (for instance, to accommodate different AFMs, or similar microscopes) without departing from the spirit and scope of the invention. It is therefore to be understood that within the scope of the appended claims the invention may be practiced other than as specifically described herein.

What is claimed is:

1. A humidity chamber suitable for use with an atomic force microscope (AFM) comprising a chamber, an integrated sample platform, a spring loaded base and a side entry port.

2. The humidity chamber of claim 1, wherein said humidity chamber comprises means for accessing an optical microscope lens.

3. The humidity chamber of claim 1, wherein said humidity chamber provides means for using an optical system to locate and focus on a probe and/or a sample positioned in said chamber.

4. A humidity chamber comprising a design configured to at least partially enclose a scanned-stylus atomic force microscope (AFM), wherein said humidity chamber comprises a chamber, an integrated sample platform, a spring loaded base and a side entry port.

5. The humidity chamber of claim 4, wherein said humidity chamber comprises means for controlling relative humidity.

6. The humidity chamber of claim 4, wherein said humidity chamber comprises means for accessing an optical system.

7. The humidity chamber of claim 4, wherein said humidity chamber comprises an AFM scanning head assembly placed within said chamber, and wherein said integrated sample platform and said spring-loaded base-plate allow samples to be loaded and unloaded without removal of the humidity chamber from the AFM scanning head assembly.

8. The humidity chamber of claim 4, wherein said chamber completely encloses one or more of an AFM head assembly, an AFM scanning probe, an optical lever detection system, an optical microscope objective lens, and a sample.

9. The humidity chamber of claim 8, wherein said integrated sample platform and spring loaded base comprise means by which samples are loaded and unloaded without removal of said humidity chamber from said AFM.

10. The humidity chamber of claim 4, wherein said humidity chamber provides an essentially air-tight fit between the humidity chamber and a scanning head assembly of said AFM.

11. The humidity chamber of claim 4, wherein said humidity chamber includes means for positioning a sample prior to scanning.

12. A humidity chamber for use with a scanning stylus atomic force microscope (AFM) comprising:
a chamber comprising an aperture fitted to allow insertion of an AFM scanning head assembly and sized to enclose at least a part of said AFM scanning head assembly;
a spring-loaded base with an integrated sample port;
a side-entry port; and
adjacent entry and exit ports which allow humid air to be delivered into the chamber, fill the chamber, and exit the chamber.

13. The humidity chamber of claim 12, wherein said chamber is essentially air-tight.

14. The humidity chamber of claim 12, wherein said chamber at least partially encloses an optical lever detection system.

15. The humidity chamber of claim 12, wherein said sample port can be detached and reattached to said chamber for unloading and loading of samples.

16. The humidity chamber of claim 12, wherein said sample port can be used to provide a snug fit between said chamber and said AFM scanning head assembly.

17. The humidity chamber of claim 12, wherein said side-entry port comprises an aperture for insertion of an optical microscope lens into said chamber.

18. The humidity chamber of claim 12, wherein a sample platform extends up from a base-plate and is inserted into the chamber.

19. The humidity chamber of claim 18, further comprising a magnet securely attached to said base-plate.

20. The humidity chamber of claim 18, wherein a locking pin secures said sample platform and said base-plate within said chamber.

* * * * *

UNITED STATES PATENT AND TRADEMARK OFFICE
CERTIFICATE OF CORRECTION

PATENT NO.      : 6,490,913 B1
DATED           : December 10, 2002
INVENTOR(S)     : Jonathan W. Martin, Edward Embree and Mark R. VanLandingham It is certified that error appears in the above-identified patent and that said Letters Patent is hereby corrected as shown below:

<u>Title page,</u>
Item [60], Related U.S. Application Data, that portion reading "May 19, 1995" should read -- May 19, 1999 --

Signed and Sealed this

Sixteenth Day of September, 2003

JAMES E. ROGAN
*Director of the United States Patent and Trademark Office*